United States Patent
Lee et al.

(10) Patent No.: US 11,566,099 B2
(45) Date of Patent: Jan. 31, 2023

(54) FURFURYL ALCOHOL-DERIVED BIFUNCTIONAL FURAN EPOXY AND METHOD FOR PRODUCING SAME

(71) Applicant: KUK DO CHEMICAL CO., LTD., Seoul (KR)

(72) Inventors: Shin Youp Lee, Gyeonggi-do (KR); Hye Seung Lee, Seoul (KR)

(73) Assignee: KUK DO CHEMICAL CO., LTD, Seoul (KR)

(*) Notice: Subject to any disclaimer, the term of this patent is extended or adjusted under 35 U.S.C. 154(b) by 279 days.

(21) Appl. No.: 17/253,554

(22) PCT Filed: May 17, 2019

(86) PCT No.: PCT/KR2019/005953
§ 371 (c)(1),
(2) Date: Dec. 17, 2020

(87) PCT Pub. No.: WO2019/245169
PCT Pub. Date: Dec. 26, 2019

(65) Prior Publication Data
US 2021/0355267 A1 Nov. 18, 2021

(30) Foreign Application Priority Data
Jun. 22, 2018 (KR) .......... 10-2018-0072241

(51) Int. Cl.
| C08G 59/04 | (2006.01) |
| C07D 407/14 | (2006.01) |
| C08G 59/02 | (2006.01) |
| C09D 163/00 | (2006.01) |

(52) U.S. Cl.
CPC .......... *C08G 59/04* (2013.01); *C07D 407/14* (2013.01); *C08G 59/022* (2013.01); *C09D 163/00* (2013.01)

(58) Field of Classification Search
CPC ...... C08G 59/02; C08G 59/022; C08G 59/04; C08G 59/5026; C08G 59/5033; C07D 307/34; C07D 407/14; C09D 163/00
See application file for complete search history.

(56) References Cited

U.S. PATENT DOCUMENTS

2012/0220742 A1* 8/2012 Cho .................. C08G 59/26
526/270

FOREIGN PATENT DOCUMENTS

| KR | 10-2011-0026664 A | 3/2011 |
| KR | 10-1561980 B1 | 10/2015 |
| KR | 10-1718568 B1 | 3/2017 |
| KR | 10-1791852 B1 | 10/2017 |
| KR | 10-1966878 B1 | 4/2019 |
| WO | WO2015-034964 | 3/2015 |

* cited by examiner

*Primary Examiner* — Megan McCulley
*Assistant Examiner* — Kimberly Thi Nguyen
(74) *Attorney, Agent, or Firm* — Culhane Meadows PLLC; Robert C. Klinger

(57) ABSTRACT

A method for producing bifunctional furan epoxy (BFFE) according to various embodiments of the present disclosure uses a bio-based monofunctional furan raw material to produce BFFE, and may include synthesizing BFFE raw material by reacting furfuryl alcohol, formaldehyde, and an acid-base mixture catalyst, and polymerizing BFFE by adding epichlorohydrin (ECH), a base catalyst, and a solvent to the BFFE raw material.

11 Claims, 1 Drawing Sheet

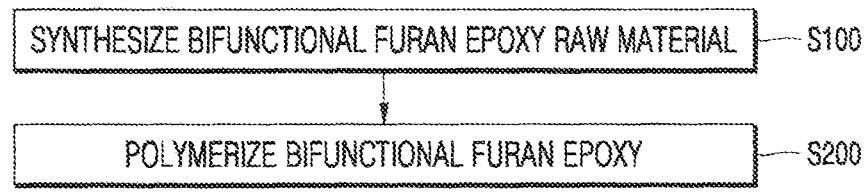

FURFURYL ALCOHOL-DERIVED BIFUNCTIONAL FURAN EPOXY AND METHOD FOR PRODUCING SAME

FIELD

The present disclosure relates to bifunctional furan epoxy (BFFE) derived from furfuryl alcohol and a method for producing the same, and more specifically, to a method for producing BFFE from monofunctional furfuryl alcohol by a one pot reaction, and BFFE produced using the method.

BACKGROUND

Petroleum-based polymer resins remain widely used as materials for various purposes, such as plastics. For example, due to advantages of having excellent adhesion, mechanical properties, and chemical resistance, and involving low shrinkage during curing, petroleum-based bisphenol-based epoxy resins are widely used in various industrial fields, such as coating, adhesives, electrics/electronics, civil engineering, and the like. Chemicals that use such a bisphenol-based epoxy resin as a main material are derived from petroleum, and as such, during preparation and use thereof, chemical substances that are harmful to the human body, such as environmental hormones, are generated. In addition, when disposed of, such petroleum-based polymer resins cause environmental pollution, such as by discharging large amounts of greenhouse gases such as carbon dioxide. In addition, as petroleum resources are gradually becoming depleted, the use of biomass-based polymer resins has been widely studied in recent years.

As bio-based materials, various materials using bio-materials such as sorbitol, butandiol, and soybean have been developed in the epoxy field. However, since these have a simple aliphatic structure, not containing a ring structure in the structure thereof, the physical properties thereof are deteriorated in comparison to existing petrochemicals.

Meanwhile, as a bio-epoxy having a ring in the structure thereof, studies have been conducted on an isosorbide epoxy that uses isosorbide instead of bisphenol A, and have shown that such an isosorbide epoxy is both environmentally friendly and has similar properties to petrochemical-based epoxies.

By contrast, in the case of furan epoxies, although a furfuryl alcohol epoxy, which is a monofunctional furan epoxy, exists, bifunctional furan epoxy (hereinafter, BFFE) is not commercially available. Previous research has been conducted on the preparation of a bishydroxymethyl furan (hereinafter, BHMF)-based epoxy, but this research focuses only on epoxidation of the raw material and does not include the production of BHMF raw material, or the manufacturing process of the BHMF raw material is overly complicated, and thus economically infeasible. Accordingly, the existing techniques are faced with various limitations in terms of commercial mass production of BFFE.

SUMMARY

In order to address the limitations described above, the inventors of the present disclosure have, as a result of continuous research on an economical and efficient method for synthesizing bifunctional furan epoxy (BFFE), developed a method capable of synthesizing BFFE, raw material from a monofunctional raw material using a one pot reaction, and economically producing BFFE by continuously using the synthesized BFFE raw material.

A method for producing bifunctional, furan epoxy (BFFE) according to various embodiments of the present disclosure may include synthesizing BFFE raw material by reacting furfuryl alcohol, formaldehyde, and an acid-base mixture catalyst, and polymerizing BFFE by adding epichlorohydrin (ECH), a base catalyst, and a solvent to the BFFE raw material.

Through various embodiments of the present disclosure, BFFE can be easily synthesized using furfuryl alcohol, which is a biomass-derived pentose raw material. The method for producing BFFE according to various embodiments of the present disclosure is capable of simply and economically producing BFFE by using raw materials that are easily accessible industrially, and the method thus has significant industrial value. According to the present disclosure, since the entire process for producing the BFFE can be performed as a one pot reaction, there is a high possibility of commercialization. In addition, since the BFFE can be produced using raw materials derived from non-edible biomass or waste biomass, positive environmental effects can be expected in that a low-carbon polymer is produced.

BRIEF DESCRIPTION OF THE DRAWINGS

The above and other aspects, features, and advantages of the present disclosure will become apparent from the detailed description of the following aspects in conjunction with the accompanying drawings, in which:

FIG. 1 is a flowchart showing the processes of a method for producing bifunctional furan epoxy (BFFE) according to various embodiments of the present disclosure.

BEST MODE

A method for producing bifunctional furan epoxy (BFFE) of the present disclosure, the method using a bio-based monofunctional furan raw material to produce BFFE, may include synthesizing. BFFE raw material by reacting furfuryl alcohol, formaldehyde, and an acid-base mixture catalyst, and polymerizing BFFE by adding epichlorohydrin (ECH), a base catalyst, and a solvent to the BFFE raw material. The solvent may include one or more solvents selected from the group consisting of ether based alcohols including ethylene glycol methyl ether, propylene glycol methyl ether (PGME), and butylene glycol methyl ether.

DETAILED DESCRIPTION

Hereinafter a method for producing bifunctional furan epoxy (BFFE) according to the present disclosure will be described in detail with reference to the following detailed examples. However, the following description is not intended to limit the present disclosure to specific embodiments, and the present disclosure should be understood as including all modifications, equivalents, and replacements that fall within the spirit and technical scope thereof. In addition, the various constituent elements used in the detailed description should not be understood to be limited by the terms used therefor. Furthermore, the terms used in the detailed description, including technical or scientific terms, have the same meaning as would be commonly understood by a person skilled in the art in the technical field of the present disclosure, unless specifically defined otherwise.

Hereinbelow, examples of the present disclosure will be described in greater detail with reference to the accompanying drawing.

FIG. 1 is a flowchart showing the processes of a method for producing BFFE according to various embodiments of the present disclosure.

Referring to FIG. 1, the method for producing BFFE according to various embodiments of the present disclosure may include steps of synthesizing BFFE raw material using furfuryl alcohol (S100), and polymerizing BFFE (S200).

In the step of synthesizing the BFFE raw material (S100), furfuryl alcohol, formaldehyde, and an acid-base mixture catalyst may be reacted.

Furfuryl alcohol, which is the raw material precursor, is commonly obtained by reducing furfural. The raw material precursors of the present disclosure, furfural and furfuryl alcohol, are currently produced on an industrial scale, and have a price such that they can be commercially used as raw materials.

Furfural is a substance produced during acid hydrolysis of lignocellulosic biomass, and is mainly produced through a dehydration reaction of an aldopentose, such as xylose. In this respect, the BFFE raw material is a biomass-based furan monomer.

Furfuryl alcohol, the main raw material, and furfural, the precursor thereof, are commercialized products (400,000 tons of which are produced worldwide per year), and the raw material biomasses for producing these are agricultural by-products such as corncob and sugarcane bagasse. The furfuryl alcohol of the present disclosure may preferably be a furfuryl alcohol derived from hemicellulose. That is, in the present disclosure, the BFFE raw material and the BFFE can be prepared using furfuryl alcohol derived from non-edible biomass or waste biomass.

Meanwhile, the formaldehyde that is reacted with the furfuryl alcohol may be liquid formaldehyde. For example, the formaldehyde may be formalin.

The acid-base mixture catalyst, which is a mixture of an organic acid and its conjugate base, maintains a constant pH in the reactor, and promotes a hydroxymethylation reaction of the furfuryl alcohol raw material. Such a pH control function maintains the main reaction rate, and at the same time suppresses the formation of a polymeric component due to side reactions.

As the organic acid of the acid-base mixture catalyst, one or more selected from the group consisting of acetic acid, acetoacetic acid, adipic acid, azelaic acid, n-butyric acid, benzoic acid, citric acid, cyclohexanecarboxylic acid, enolpyruvic acid, formic acid, fumaric acid, galactaric acid, galactonic acid, glucaric acid, gluconic acid, glutaric acid, glyceric acid, glyceric acid 2-phosphate, glycolic acid, glyoxylic acid, hydroxybutyric acid, n-hexanoic acid, isobutyric acid, isophthalic acid, itaconic acid, lactic acid, levulinic acid, italic acid, methyl malonic acid, n-pentanonic acid, pimelic acid, propionic acid, succinic acid, suberic acid, tartaric acid, and terephthalic acid, as organic acids having a carboxylic group, may be used alone or in combination.

The organic acid may preferably be propionic acid, and sodium propionate may be used as its conjugate base.

In the step of synthesizing the BFFE raw material (S100), the furfuryl alcohol, formaldehyde, and acid-base mixture catalyst may be reacted for 2 to 8 hours at a temperature of 100° C. to 200° C. and under atmospheric pressure. Thereafter, a process of neutralizing the reaction solution may be further performed by adding liquid sodium hydroxide in a molar ratio of 1:1 to the amount organic acid in the acid-base mixture catalyst. In addition, a process of distilling unreacted furfuryl alcohol under reduced pressure may be further performed.

Thereafter, in the step of polymerizing the BFFE (S200), epichlorohydrin (ECH), a base catalyst, and a solvent may be added to the synthesized BITE raw material so as to synthesize BFFE. By adding the ECH, the base catalyst and solvent immediately after the BFFE raw material is synthesized, the whole process can be performed as a one pot reaction. Accordingly, the process is simple and economical, and can thus be applied commercially.

The ECH may be added in a molar ratio of 2:1 to 10:1 to the —OH content of the BFFE raw material.

As the base catalyst, one or more selected from the group consisting of sodium hydroxide (NaOH), potassium hydroxide (KOH), calcium hydroxide ($Ca(OH)_2$), ammonium hydroxide ($NH_4OH$), and magnesium hydroxide ($Mg(OH)_2$) may be used, alone or in combination. The base catalyst may preferably be sodium hydroxide. The base catalyst may be added dropwise, at least twice. For example, after a pre-reaction is first carried out by dropping the base catalyst in a molar ratio of 0.05:1 to 0.5:1 to the –OH content of BFFE raw material, the main reaction may be carried out by adding the base catalyst in a molar ratio of 0.5:1 to 2:1 to the –OH content of the BFFE raw material.

The solvent may include one or more solvents selected from the group consisting of ether based alcohols including ethylene glycol methyl ether, ethylene glycol ethyl ether, propylene glycol methyl ether (PGME), propylene glycol ethyl ether, butylene glycol methyl ether, and butylene glycol ethyl ether. The solvent may preferably be propylene glycol methyl ether (PGME). The solvent may be added in an amount of 20 phr to 200 phr relative to the BFFE raw material. In the present disclosure, by introducing a solvent such as those specified, it is possible to suppress the formation of the polymeric component during BFFE synthesis.

In the step of polymerizing the BFFE (S200), an epoxy represented by the following Formula 1 and an epoxy represented by the following Formula 2 may be obtained.

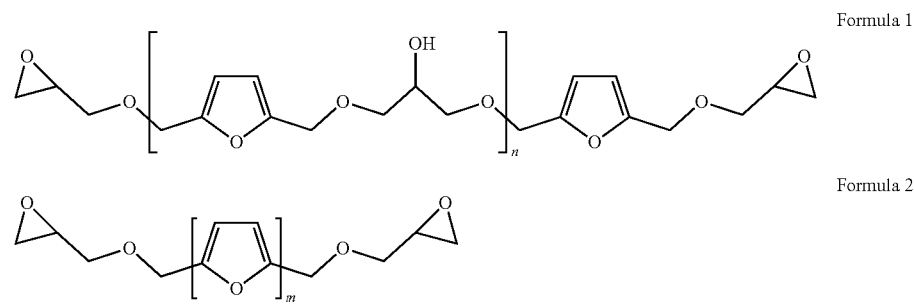

Formula 1

Formula 2

Here, $n \geq 0$ and $m \geq 1$.

The epoxy of Formula 1 and the epoxy of Formula 2 may include a monomeric component and a polymeric component. Specifically, the monomeric component is an epoxy wherein n=0 in Formula 1 or m=1 in Formula 2. The polymeric component is an epoxy wherein n>0 in Formula 1 and m>1 in Formula 2. More specifically, in the step of polymerizing BFFE (S200), a mixed resin of monomeric BITE (n=0 in Formula 1 or m=1 in Formula 2), polymeric BFFE (n>0 in Formula 1), and polymerized furan bifunctional epoxy (m>1 in Formula 2) can be obtained. In the present disclosure, by introducing a solvent as specified above, formation of the polymeric BFFE (n>0 in Formula 1) and the polymerized furan bifunctional epoxy (m>1 in Formula 2) is suppressed, and the monomeric component (n=0 in Formula 1 or m=1 in Formula 2) may be obtained in a yield of 50% or more.

After completion of the reaction of the BFFE raw material, the ECH, the base catalyst, and the solvent, unreacted ECH and solvent may be distilled and recovered to obtain a mixture of BFFE and salt. Here, the recovered ECH can be reused. Thereafter, an organic solvent and water are added and separated to recover the solvent portion, and the salt may be removed by discarding the aqueous solution layer. In addition, the solvent of the solvent portion may be distilled and removed, and BFFE can be obtained. The recovery rate of BFFE may be 50% or more.

Hereinafter, the method for producing BFFE of the present disclosure will be described in more detail with reference to the Comparative Examples and Examples that follow.

Example 1 (One Pot Reaction with PGME)

According to the relative weight ratios of the input raw materials shown in Table 1 below, furfuryl alcohol, formaldehyde, propionic acid, and sodium propionate were collectively added to the reactor, and then reacted for 5 hours under atmospheric pressure while maintaining a temperature of 125° C. Thereafter, to recover the unreacted furfuryl alcohol after neutralizing the reaction solution by adding liquid NaOH in a molar ratio of 1:1 to the amount of propionic acid, a reddish brown crystalline solid (based on room temperature) was prepared by performing low temperature recovery of the furfuryl alcohol by reducing the pressure to 20 torr while maintaining a temperature of 90° C.

The prepared reddish brown solid can be used as a raw material for producing BFFE in one pot. ECH in a molar ratio of 5:1 to the OH content in the solid, and PGME the same amount as the solid, were added. After the reaction solution was stirred and heated to 75 degrees, a pre-reaction was carried out by dropping NaOH in a molar ratio of 0.1:1 to the OH content over 1 hour. Thereafter, after the reaction system was reduced in pressure to 240 torr while maintaining the temperature, the main reaction was carried out by dropping NaOH in a molar ratio of 1:1 to the OH content over 200 minutes. Water produced during the reaction was continuously removed. Thereafter ECH and PGME were distilled and recovered at 130 degrees and 20 torr to obtain BFFE. Thereafter MEK and water were added and separated to recover the organic layer, and water-soluble impurities were removed by discarding the aqueous solution layer. Finally, the MEK of the solvent portion was distilled and removed at 130° C. and 20 torr (based on a final recovery condition) to obtain BFFE. Regarding the molecular weight distribution of the recovered BFFE (recovery rate 72.8%), the content was 76.4%, and it was thus possible to obtain a predominantly monomeric epoxy.

Comparative Example 1 (One Pot Reaction Without PGME)

Comparative Example 1 was conducted in the same manner as Example 1, except with PGME excluded from the additional input raw materials.

TABLE 1

| | Example 1 | Comparative Example 1 |
|---|---|---|
| Initial input raw materials (g) | Furfuryl alcohol 1000<br>Formalin (37%) 81.1<br>Propionic acid 40<br>Sodium propionate 2 | Same |
| First reaction conditions | 125° C., 760 torr, 5 hr | Same |
| Post process | 1) Neutralization<br>2) Distillation of unreacted raw materials | Same |
| Additional input raw materials (g) | Epichlorohydrin 825<br>PGME 125.2<br>NaOH 7.1 (pre-reaction)<br>NaOH 71.4 (main reaction) | Epichlorohydrin 825<br>NaOH 7.1 (pre-reaction)<br>NaOH 71.4 (main reaction) |
| Second reaction conditions | 75° C., 240 torr, 200 min | Same |
| Post process | 1) ECH recovery<br>2) separation (MEK/water)<br>3) MEK recovery | Same |
| BFFE yield (g) | 163.8 | 97.9 |
| Content of the yield (GPC area %) | Monomeric component (n = 0 or m = 1) 76.4<br>Polymeric component (n > 0 and m > 1) 23.6 | Monomeric component (n = 0 or m = 1) 72.4<br>Polymeric component (n > 0 and m > 1) 27.6 |
| Monomeric component yield (g) (BFFE yield × monomeric component content) | 125.1 | 70.9 |

Referring to Table 1, in the case of Comparative Example 1 in which PGME was removed in the epoxidation step, it can be seen that most of the polymeric component generated during the reaction (n>0 in Formula 1 and m>1 in Formula 2) was precipitated and removed in the post process, and the total amount of BFFE obtained and the amount of the monomeric component obtained were significantly reduced, even though the other reaction conditions were the same as in Example 1. That is, only 56.7% of the monomeric component obtained in Example 1 was obtained in Comparative Example 1.

Application Example 1 (BFFE Coating)

As an epoxy resin, physical properties of the BFFE of Example 1 as a coating agent were confirmed. The epoxy resin composition of the present disclosure was prepared by mixing with isophorone diamine (IPDA) as a curing agent. The resin composition was coated on an iron specimen with a thickness of 150 mm, and then cured at 25° C. for 48 hours, followed by curing at 50° C. for 4 hours.

Application Example 2

A cured epoxy resin product was prepared in the same manner as in Application Example 1, except that m-xylene diamine (MXDA) was used as the curing agent.

Comparative Example 2 (Preparation of General-Purpose Bisphenol A-Type Epoxy Resin Composition and Cured Product)

A cured epoxy resin product was prepared in the same manner as in Application Example 1, except that a general-purpose epoxy resin (Liquid Bisphenol A type, YD-128 (Kukdo Chemical)) was used.

Comparative Example 3

A cured epoxy resin product was prepared in the same manner as in Application Example 2, except that a general-purpose epoxy resin (Liquid Bisphenol A type, YD-128 (Kukdo Chemical)) was used.

The components and contents of the epoxy resin compositions of Application Example 1. Application Example 2, Comparative Example 2, and Comparative Example 3 are shown in Table 2 below.

TABLE 2

|  | Application Example 1 | Application Example 2 | Comparative Example 2 | Comparative Example 3 |
|---|---|---|---|---|
| BFFE of Example 1 | 100 | 100 | — | — |
| General-purpose epoxy | — | — | 100 | 100 |
| IPDA | 27.5 | — | 22.8 | — |
| MXDA | — | 22.0 | — | 18.2 |

Gel time, adhesiveness, pencil hardness, glass transition temperature, and Shore-D were respectively measured for the epoxy resin compositions of Table 2 and the results thereof are as shown in Table 3 below.

TABLE 3

|  | Application Example 1 | Application Example 2 | Comparative Example 2 | Comparative Example 3 |
|---|---|---|---|---|
| Gel time [1] | 15 min | 25 min | 55 min | 90 min |
| Adhesiveness [2] | 100/100 | 100/100 | 80/100 | 11/100 |
| Pencil hardness [3] | F | F | HB | HB |
| Glass transition temperature (Tg) [4] | 60.9 | 39.9 | 152.5 | 121.6 |
| Shore-D [5] | 80.7 | 47.4 | 93.2 | 93.1 |

[1] Gel time: The epoxy and curing agent were quantified, mixed for 2 minutes, stirred, and cured in a laboratory controlled at 23° C. and 50% RH. The progress of the reaction was observed visually, and the time taken to change from liquid to gel form was recorded.
[2] Adhesion: On the coated substrate, cracks were drawn with a knife to form a grid of 100 squares, and a sensitive tape was attached on top of the grid and then quickly peeled off, to show the number of squares remaining on the substrate. (ASTM D3359)
[3] Pencil hardness: A pencil of which the tip was shaped to 90° was maintained at a 45° angle, and moved by 2 inches or more on the coated surface with a 1 Kg load. If the coating was damaged or deformed, measurements were made with pencils having the subsequent lower hardness levels until the coating was no longer deformed (ASTM D3364).
[4] Glass transition temperature: Glass transition temperature (Tg) was measured through DSC analysis.
[5] Shore-D: The surface of life cured sample was flattened using a metal file. After curing for 7 days in a laboratory controlled at 23° C. and 50% RH, the D hardness value was measured 10 times using a digitest II Gelomat hardness tester, and the average value was recorded.

As shown in Table 3 above, the BFFE epoxy cured products of Example 1 (Application Example 1 and Application Example 2) had a faster curing speed compared to the general-purpose epoxy resin cured products (Comparative Example 2 and Comparative Example 3), and showed excellent results in terms of adhesion and pencil hardness. By contrast, due to the flexible repeating unit structure, the glass transition temperature and Shore-D value of the BFFE epoxy cured products showed relatively low values. Overall, when applied alone or mixed with an existing general-purpose epoxy, the BFFE epoxy produced by the present disclosure can be put to good use in fields requiring fast curing, high adhesion, and scratch resistance.

While the present disclosure has been described above in relation to its embodiments, it is to be understood that these are only examples and do not limit the present disclosure, and those skilled in the art in the field to which the present disclosure belongs will understand that various modifications and applications not described above are possible without departing from the essential characteristics of the present disclosure. For example, each component specifically described in the embodiments can be modified, and implemented as modified. Further, differences related to these modifications and applications are to be understood as being included in the scope of the present disclosure defined in the appended claims.

INDUSTRIAL APPLICABILITY

The present disclosure is capable of synthesizing bifunctional furan epoxy (BFFE) raw material from a monofunctional raw material using a one pot reaction, and economically producing BFFE by continuously using the synthesized BFFE raw material.

What is claimed is:

1. A method for producing bifunctional furan epoxy (BFFE), the method using a bio-based monofunctional furan raw material to produce BFFE, and the method comprising:
   synthesizing BFFE raw material by reacting furfuryl alcohol, formaldehyde, and an acid-base mixture catalyst; and
   polymerizing BFFE by adding epichlorohydrin (ECH), a base catalyst, and a solvent to the BFFE raw material,
   wherein the solvent comprises one or more solvents selected from a group consisting of ether based alcohols comprising ethylene glycol methyl ether, propylene glycol methyl ether (PGME), and butylene glycol methyl ether.

2. The method of claim 1, wherein the formaldehyde is liquid formaldehyde.

3. The method of claim 2, wherein the liquid formaldehyde comprises formalin.

4. The method of claim 1, wherein the acid-base mixture catalyst is a mixture of an organic acid and a conjugate base of the organic acid.

5. The method of claim 2, wherein the organic acid is an organic acid having a carboxylic group, comprising one or more selected from a group consisting of acetic acid, acetoacetic acid, adipic acid, azelaic acid, n-butyric acid, benzoic acid, citric acid, cyclohexanecarboxylic acid, enolpyruvic acid, formic acid, fumaric acid, galactaric acid, galactonic acid, glucaric acid, gluconic acid, glutaric acid, glyceric acid, glyceric acid 2-phosphate, glycolic acid, glyoxylic acid, hydroxybutyric acid, n-hexanoic acid, isobutyric acid, isophthalic acid, itaconic acid, lactic acid, levulinic acid, malic acid, methyl malonic acid, n-pentanonic acid, pimelic acid, propionic acid, succinic acid, suberic acid, tartaric acid, and terephthalic acid, used alone or in combination.

6. The method of claim 1, wherein the base catalyst comprises one or more selected from a group consisting of sodium hydroxide (NaOH), potassium hydroxide (KOH), calcium hydroxide ($Ca(OH)_2$), ammonium hydroxide ($NH_4OH$), and magnesium hydroxide ($Mg(OH)_2$), used alone or in combination.

7. The method of claim 1, wherein in the polymerizing the BFFE, an epoxy of the following Formula 1 and an epoxy of the following Formula 2 are obtained:

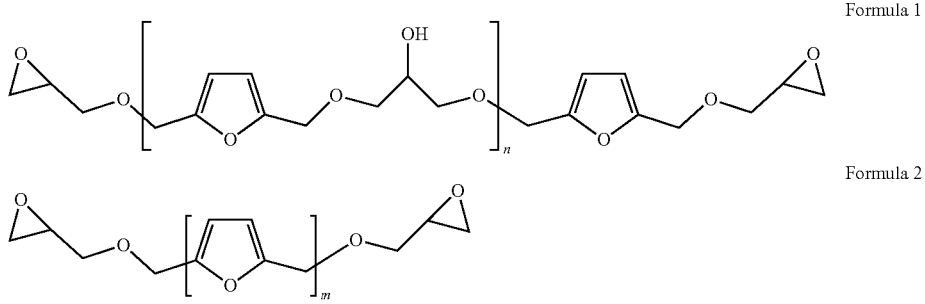

Formula 1

Formula 2 wherein n≥0 and m≥1.

8. The method of claim 7, wherein the BFFE comprises:
a monomeric component wherein n=0 in Formula 1 or m=1 in Formula 2; and
a polymeric component wherein n>0 in Formula 1 and m>1 in Formula 2,
wherein the monomeric component is obtained in a yield of 50% or more, and formation of the polymeric component is suppressed.

9. The method of claim 1, wherein the reaction is performed as a one pot reaction.

10. Bifunctional furan epoxy (BFFE) produced according to the method of claim 1.

11. A method for producing bifunctional furan epoxy (BFFE), the method using a bio-based monofunctional furan raw material to produce BFFE, and the method comprising:
synthesizing BFFE raw material by reacting furfuryl alcohol, formaldehyde, and an acid-base mixture catalyst; and
polymerizing BFFE by adding epichlorohydrin (ECH), a base catalyst, and a solvent to the BFFE raw material,
wherein the polymerizing the BFFE comprises:
conducting a first reaction by adding ECH, a base catalyst, and a solvent to the BFFE raw material; and
conducting a second reaction by reducing reaction system pressure and then additionally adding the base catalyst.

* * * * *